US008229546B2

(12) United States Patent
Falkén et al.

(10) Patent No.: US 8,229,546 B2
(45) Date of Patent: Jul. 24, 2012

(54) MICRODIALYSIS CATHETER AND A METHOD OF MAKING A MICRODIALYSIS CATHETER

(75) Inventors: Henrik Falkén, Lidingö (SE); Jan Liska, Stockholm (SE)

(73) Assignee: CMA Microdialysis AB, Solna (SE)

( * ) Notice: Subject to any disclaimer, the term of this patent is extended or adjusted under 35 U.S.C. 154(b) by 33 days.

(21) Appl. No.: 12/446,098

(22) PCT Filed: Oct. 17, 2007

(86) PCT No.: PCT/SE2007/050747
§ 371 (c)(1),
(2), (4) Date: Mar. 9, 2010

(87) PCT Pub. No.: WO2008/048183
PCT Pub. Date: Apr. 24, 2008

(65) Prior Publication Data
US 2010/0204565 A1    Aug. 12, 2010

Related U.S. Application Data

(60) Provisional application No. 60/829,883, filed on Oct. 18, 2006.

(30) Foreign Application Priority Data

Oct. 18, 2006   (SE) ...................................... 0602199

(51) Int. Cl.
*A61M 25/14*   (2006.01)
*A61B 8/12*    (2006.01)
*A61B 6/12*    (2006.01)
*B29C 47/20*   (2006.01)

(52) U.S. Cl. .................. 600/424; 604/6.16; 264/177.14
(58) Field of Classification Search ................ 604/29, 604/6.16; 600/424; 264/177.14
See application file for complete search history.

(56) References Cited

U.S. PATENT DOCUMENTS

| | | | | |
|---|---|---|---|---|
| 3,985,655 A * | 10/1976 | Miller, III | ............... | 210/321.74 |
| 4,031,010 A * | 6/1977 | Nose | .............................. | 210/202 |
| 5,441,481 A * | 8/1995 | Mishra et al. | .................. | 604/29 |
| 5,640,954 A | 6/1997 | Pfeiffer et al. | | |
| 5,810,789 A | 9/1998 | Powers et al. | | |
| 5,928,744 A * | 7/1999 | Heilmann et al. | ........... | 428/36.6 |
| 6,264,627 B1 * | 7/2001 | Liska et al. | ..................... | 604/29 |

(Continued)

OTHER PUBLICATIONS

Extended European Search Report from corresponding EP 07835332.3.
Backstrom et al, "Monitoring of Porcine Myocardial Ischemia and Reperfusion by Intravasal Microdialysis", Scand Cardiovasc J, Taylor & Francis Healthsciences, 36:27-34 (2002).

(Continued)

*Primary Examiner* — Jackie Ho
*Assistant Examiner* — Michael J Anderson
(74) *Attorney, Agent, or Firm* — Porter Wright Morris & Arthur

(57) ABSTRACT

The invention relates to a microdialysis catheter comprising a multilumen tube (10) and a membrane (11), said tube exhibiting at least two longitudinally arranged inner channels (13, 14), said channels extending from a proximal (20) end of the tube to the distal end (21) of the tube, whereat through-holes (12,15) are provided, one from each of said at least two channels to the outside of said tube, said channels (13,14) blocked for passage of liquid distally of the respective through-holes, a tubular membrane (11) arranged circumferentially around the tube (10) such as to cover the at least two through -holes (12,15), said membrane is sealingly fastened (22) to the tube thereby forming a dialysis chamber (18) between the tube and the membrane.

13 Claims, 2 Drawing Sheets

U.S. PATENT DOCUMENTS

| | | | |
|---|---|---|---|
| 6,346,090 B1 * | 2/2002 | Liska et al. | 604/29 |
| 6,811,542 B2 * | 11/2004 | Liska et al. | 604/29 |
| 2003/0060751 A1 * | 3/2003 | Haindl | 604/27 |
| 2003/0217966 A1 * | 11/2003 | Tapsak et al. | 210/500.21 |
| 2005/0015044 A1 | 1/2005 | Harttig et al. | |
| 2008/0234563 A1 * | 9/2008 | Regittnig | 600/365 |

OTHER PUBLICATIONS

Rojdmark et al, "Comparing Metabolism During Ischemia and Reperfusion in Free Flaps of Different Tissue Composition", Eur J Plast Surg, 24:349-355 (2002).

\* cited by examiner

MICRODIALYSIS CATHETER AND A METHOD OF MAKING A MICRODIALYSIS CATHETER

RELATED APPLICATION

This application is a 371 of PCT/SE2007/050747 filed Oct. 17, 2007 and claims priority under 35 U.S.C. §119 of U.S. Application Ser. No. 60/829,883 filed Oct. 18, 2006.

FIELD OF THE INVENTION

The present invention generally relates to a microdialysis catheter for insertion into a blood vessel and a method for making the same.

BACKGROUND OF THE INVENTION

Microdialysis is used to monitor the interstitial fluid in various body organs with respect to local metabolic changes. It may also be used in blood vessels. Such a microdialysis catheter is known from e.g. U.S. Pat. No. 6,346,090 Liska et al. and U.S. Pat. No. 6,811,542 and U.S. Pat. No. 6,264,627 also in the name of Liska et al.

U.S. Pat. No. 6,811,542 uses a third transport channel in order to speed up the transport of the dialysate (the perfusate as it has passed through the dialysis chamber), which is a problem the present invention seeks to solve. The perfusate from the third channel complicates the tests made on the dialysate as well as the pumping techniques.

The invention also seeks to build a catheter which compared to the one in U.S. Pat. No. 6,346,090 is easier to build.

SUMMARY OF THE INVENTION

It is an object of the invention to provide a catheter intended for insertion in e.g. a blood vessel for performing blood analyses through microdialysis. The catheter must understandably have small dimensions and the membrane must be supported in a manner such as to provide a stable and safe device. The catheter must show flexibility such as to form itself to the inside of a blood vessel and also to endure the passage through a vessel to the predetermined point where the analysis is to take place.

The present invention thus relates to a microdialysis catheter comprising a multilumen tube and a membrane, said tube exhibiting at least two longitudinally arranged inner channels, said channels extending from a proximal end of the tube to the distal end of the tube, whereat through-holes are provided, one from each of said at least two channels to the outside of said tube, said channels blocked for passage of liquid distally of the respective through-holes, a tubular membrane arranged circumferentially around the tube such as to cover the at least two through-holes, said membrane is sealingly fastened to the tube thereby forming a dialysis chamber between the tube and the membrane.

A further object of the invention is to be able to guide the catheter during the passage. According to the invention this is accomplished by providing a further channel in the multilumen tube, said further channel extending between the proximal end of the tube to the distal end of the tube, said further channel adapted to house guide means.

Still a further object of the invention is to give the possibility of measuring other parameters, such as blood pressure using the catheter.

According to the invention this is accomplished by providing a further channel in the multilumen tube, said further channel extending between the proximal end of the tube to the distal end of the tube, said further channel adapted to house pressure measurement means and/or sampling/delivering means.

Further objects of the invention are attained in that the tube comprises extruded biocompatible polymeric material.

Still a further object of the invention is attained by the tubular membrane being so arranged such as to have the selective layer on the outer circumference of the same.

Still a further object of the invention is attained by the membrane having a wall thickness of approx. 20-100 µm, preferably 30 to 80 µm.

Still a further object of the invention is attained by the inner diameter of the tubular membrane being approx. 1000-3000 µm, preferably 1000-2000 µm.

A still further object of the invention is to be able to position the catheter, and to accurately determine the position of the catheter, which object according to the invention can be attained by providing means for detection of the position of the catheter in the catheter, said means responsive to ultra sound while using the same for microdialysis purposes, or by providing means for detection of the position of the catheter in the catheter, said means imparting opaqueness to X-rays to the catheter such that it is detectable using X-rays while using the catheter for microdialysis purposes.

The invention also pertains to a method of making such a catheter device as claimed in claims 1-8.

Microdialysis performed in a blood vessel requires special measures, especially when long guidable catheters are used. In order to be useful the catheter needs to provide microdialysis samples with high accuracy and with small delay times.

Another reason is that the environment, blood, poses special problems in making sure that the microdialysis actually can take place and the membrane used functions during the use of the catheter. There is always the danger of the membrane being clogged by blood components. The insertion into blood vessels requires that the catheter is flexible and that the frail membrane is supported such that it can withstand the forces applied to the catheter during insertion and also any strain applied within the blood vessel emanating from muscle etc situated around the blood vessel.

It is also extremely important the catheter does not break during use, and thereby leaving traces of the catheter in the vessel.

The invention also relates to a method of making a microdialysis catheter wherein the method comprises extruding a multilumen tube said tube exhibiting at least two longitudinally arranged inner channels, said channels extending from a proximal end of the tube to the distal end of the tube, providing in said at least two channels through-holes one from each of said at least two channels to the outside of said tube, blocking said channels for passage of liquid distally of the respective through-holes, arranging a tubular membrane circumferentially around the tube such as to cover the at least two through-holes, sealingly fastening said membrane to the tube thereby forming a dialysis chamber between the tube and the membrane.

The method also comprises that at least one further channel in the tube is provided during the extrusion.

BRIEF DESCRIPTION OF THE DRAWINGS

The objects and advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

Figure 1:
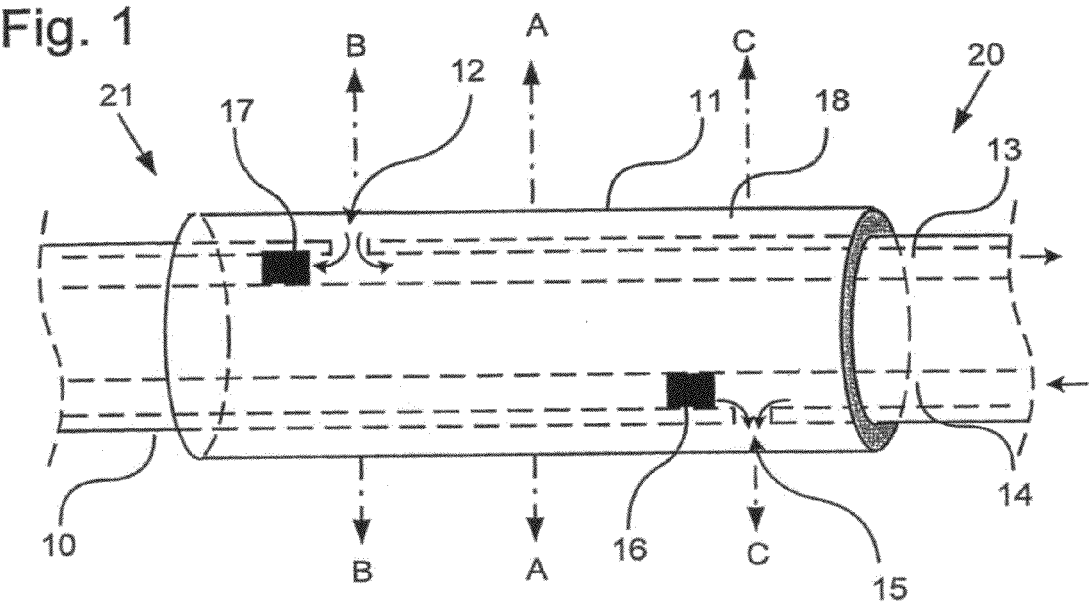
FIG. 1 shows a generalised device according to the invention.

Thus, the invention relates to a microdialysis catheter comprising a multilumen tube 10 and a membrane 11, said tube exhibiting at least two longitudinally arranged inner channels 13,14, said channels extending from a proximal end 20 of the tube to the distal end 21 of the tube, whereat through-holes 12,15 are provided, one from each of said at least two channels to the outside of said tube, said channels 13,14 blocked for passage of liquid distally of the respective through-holes, a tubular membrane 11 arranged circumferentially around the tube 10 such as to cover the at least two through-holes 12,15, said membrane is sealingly fastened 22 to the tube thereby forming a dialysis chamber 18 between the tube and the membrane.

Referring now to FIG. 1, this illustrates in a side view an exemplary device according to the invention.

In FIG. 1 is shown the (main tube) multilumen catheter 10 in the area where a micro-porous membrane 11 is arranged. Through the tube 10 there are two flow channels 13, 14 arranged in the longitudinal direction of the tube. Through-flow holes 12, 15 are arranged from the flow channels to the outside of the tube 10 in the section of the same covered by a micro-porous tube-formed membrane 11 arranged circumferentially of the tube. Both ends of the tube-formed membrane are glued (cf. FIG. 3) (21,22) or in any other feasible manner fastened/attached to the outside of the tube 10 forming a dialysis chamber device 18 between the membrane and the tube. The proximal end of the device is indicated at 20 and the distal end of the device is indicated at 21.

The perfusate, the liquid used in the microdialysis, enters the in-flow channel 14 and reaches the distal end of the channel where a plug 16 or the like is arranged stopping the further flow through the channel and the perfusate then exits the channel through the through-hole 15 and enters the chamber 18. The perfusate after having passed through the chamber 18 enters the return-flow channel 13 through the through-hole 12 for further passage out of the device. The channel 13 likewise exhibits a plug 17 on the distal side of the through-hole 12 forcing the perfusate/dialysate out from the catheter.

The plugs 16 and 17, as clearly can be understood from the preceding paragraph, has the sole purpose of defining the distal end of the flow channels 13, 14. It should be noted that the above describe flow pattern may be reversed.

The plugs 16, 17 are placed distally of the through-holes 15, 12. They may be placed near the through-holes, some distance away from the through-holes, 15, 12 or far away from the through-holes 15, 12, i.e. near the distal end 21 of the device. However, it is important that the plugs are placed on the distal side from the holes.

Figure 2:
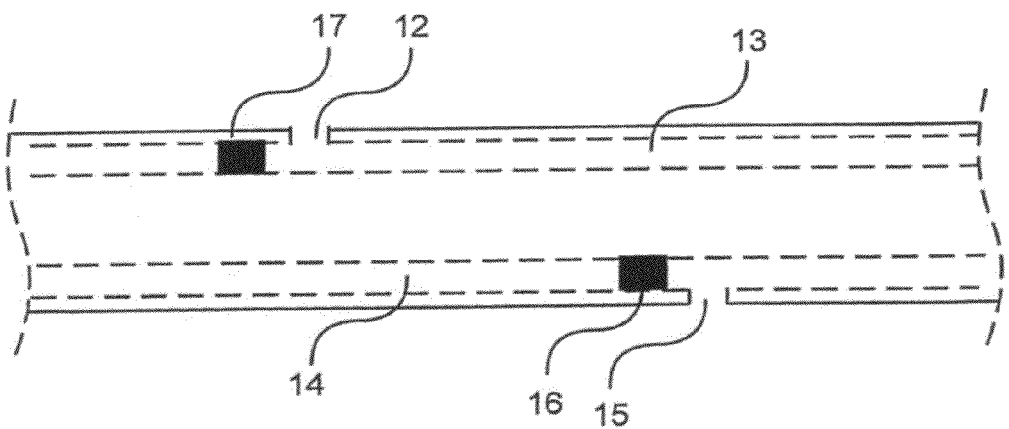
FIG. 2 shows schematically the two-channel catheter used for the invention.

In FIG. 2 the tube in FIG. 1 is shown without the membrane in order to facilitate reading of FIG. 1. The tube 10 is shown with channels 13 and 14 with respective plug 17 and 16. In other embodiments of the invention the plug may be substituted for by any means of stopping the flow in the channel and forcing the perfusate to enter the dialysis chamber defined by the tube and the membrane.

Figure 3:
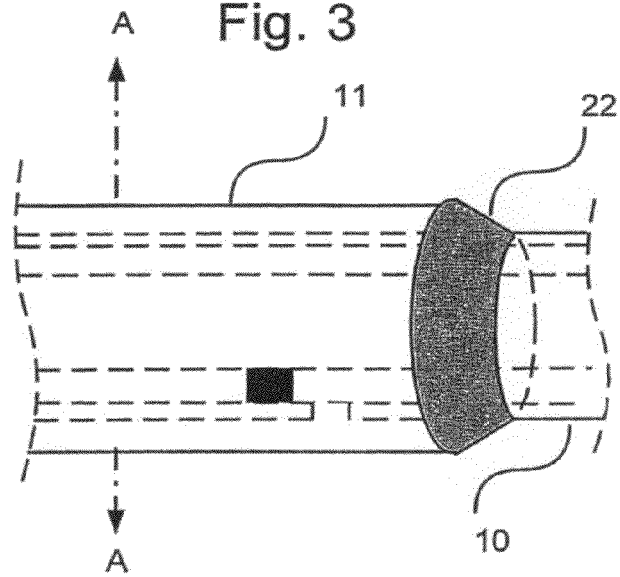
FIG. 3 shows the joint between the membrane and the catheter.

In FIG. 3 is shown the proximal end 22 of the catheter 10 and the fastening of the membrane 11 to the tube 10. The membrane according to this embodiment of the invention is glued 22 to the tube using bio-compatible glue. Glue which is UV-curable is preferred in order to shorten production time.

Figure 4A:
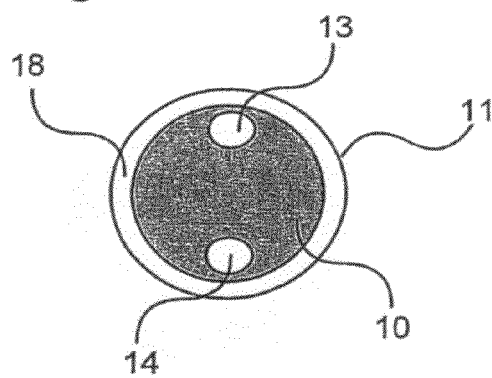
FIG. 4a shows a section along the line A-A in FIG. 1 in a first embodiment according to the invention.
Figure 4B:
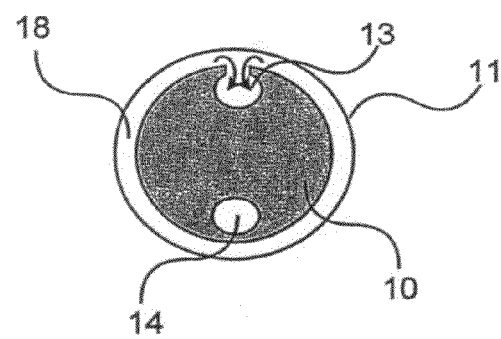
FIG. 4b shows a section along the line B-B in FIG. 1 in a first embodiment according to the invention.
Figure 4C:
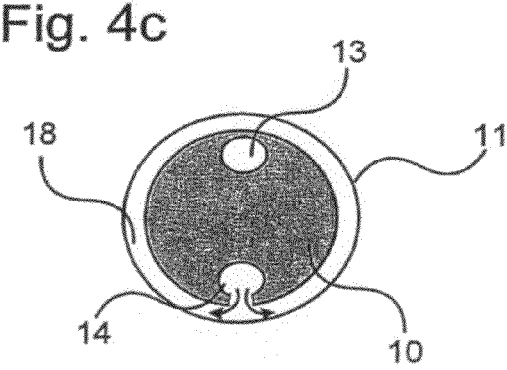
FIG. 4c shows a section along the line C-C in FIG. 1 in a first embodiment according to the invention.

In FIG. 4a the tube of FIG. 1 in a first embodiment is shown in cross-section along the line A-A indicated in FIG. 1. The membrane 11, the in-flow (14) and out-flow (13) channels of the tube 10 are shown. To illustrate the flow pattern in the dialysis chamber is shown in FIG. 4b a section along the line B-B in FIG. 1 in a first embodiment according to the invention, wherein the flow is in the direction from the dialysis chamber 18 into the out-flow channel 13 and in FIG. 4c is shown a section along the line C-C in FIG. 1 in the first embodiment according to the invention, wherein the flow is shown entering the dialysis chamber 18 from the in-flow channel 14.

Figure 4D:
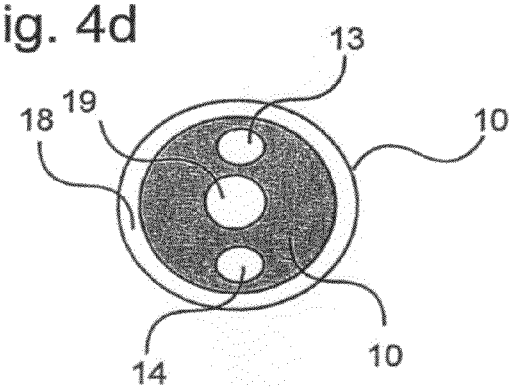
FIG. 4d shows a corresponding section to the one in FIG. 4a in a second embodiment according to the invention.

In FIG. 4d in a second embodiment there is a further channel 19 open at both ends which may be used for insertion purposes, e.g. a guiding means could be threaded into this channel 19 for guiding the catheter to the right position. The third channel may also be used for other purposes when the guide means have been removed, e.g. for taking blood samples or for measurement of the local blood pressure.

Figure 5:
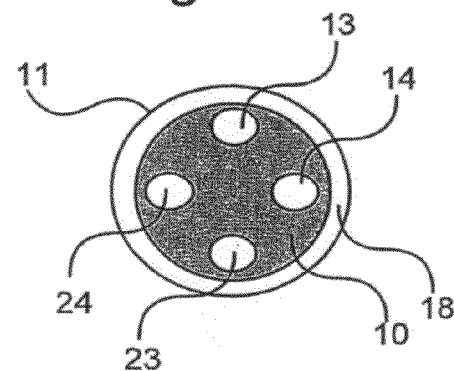
FIG. 5 shows a corresponding section to A-A in FIG. 1 in a third embodiment where the inflow-channels and out-flow channels are doubled.

In FIG. 5 a second embodiment is shown in which two inflow-channels 14, 24 and two out-flow channels 13, 23 are arranged the inflow through holes as well as the outflow through holes may be arranged at different heights and also the inflow and outflow channels are preferably 90° C. separated or the inflow channels are separated by 180°.

The number of in-flow channel/s and out-flow channel/s may be the same or may differ. According to one embodiment, the invention relates to a microdialysis catheter comprising a multilumen tube 10 and a membrane 11, said tube exhibiting longitudinally arranged inner channels 13,14 in the form of one in-flow channel 14 and one out-flow channel 13 or two in-flow channels 14, 24 and two out-flow channels 13,23, said channels extending from a proximal end of the tube to the distal end of the tube, whereat through-holes 12,15 are provided, one from each channel to the outside of said tube, said channels 13,14 blocked for passage of liquid distally of the respective through-holes, a tubular membrane 11 arranged circumferentially around the tube 10 such as to cover the through-holes 12,15, said membrane is sealingly fastened 22 to the tube thereby forming a dialysis chamber 18 between the tube and the membrane. The features described above for the catheter also relates to this embodiment such as further channels 19 and the tube may comprise biocompatible material. Further, detection means, dimensions for a catheter and features for the membrane and the selective layer disclosed in this description also relates to this embodiment.

The total in-flow rate and the total out-flow rate according to the present invention may be 1-15 µl/minute. Further, the total in-flow rate and the total out-flow rate can be 5-15

μl/minute. By "in-flow rate" is meant the in-flow rate of the liquid going through the in-flow channel/s 14, 24, then passed to the dialysis chamber 18. In the same way, by the "out-flow rate" is meant the out-flow rate of liquid going through the out-flow channel/s 13, 23, coming from the dialysis chamber 18. This liquid is also passed through the dialysis chamber 18 and have the same flow rate through the dialysis chamber 18. Thus, the dialysis chamber flow rate is 1-15 μl/minute and the dialysis chamber flow rate may be 5-15 μl/minute. The liquid is entering the dialysis chamber 18 through the through hole 15 and exiting the dialysis chamber 18 through the through hole 12. If more than one in-flow or out-flow channel is used, there are more through holes. Thus, the dialysis chamber flow rate is the same as the total in-flow rate and the total out-flow rate.

Hence, the total in-flow rate, the total out-flow rate and the dialysis chamber flow rate have the same rate, the rate is 1-15 μl/minute. Further, the rate may be 5-15 μl/minute.

The catheter may also comprise for example one in-flow channel and two out-flow channels. When more than one out-flow channel is used, the out-flow rate in each out-flow channel can be controlled by choosing the dimension on the out-flow channels. This may be of importance for certain sensors etc.

When the same number of in-flow channels and out-flow channels are used, more than two in-flow channels and two out-flow channels (as disclosed in one embodiment above) may be used, for example three in-flow channels and three out-flow channels.

The catheters disclosed above are also made by the method according to above.

Several channels which are connected with through-holes to the outside of the tube may be used, but a practical upper limit is about six channels.

Further, the catheter may be provided with detection means for localization in order to be able to non-invasively and accurately determine the position of the catheter. This can be done using ultrasound, which requires a crystal in the catheter tip responding to ultrasound. Detection can also be achieved by the use of x-ray, requiring presence of radio opaque material in the catheter.

Exemplary dimensions for a catheter for use in a blood vessel, in a vein or in an artery, could be an outer diameter of 1-3 mm, the inner diameter of the perfusate channels 50-200 μm, and the length 50-100 cm. For the membrane the inner diameter should be 30-200 μm larger than the outer diameter of the tube, preferably 30-100 μm larger than the outer diameter of the tube, the wall thickness of the membrane approximately 20-100 μm, preferably 30-80 μm and the length of the membrane 1-6 cm.

If the catheter is used in tissue the exemplary dimensions are: an outer diameter of 0.2-1 mm, the inner diameter of the channels 50-200 μm and the length 5-20 cm. For the membrane the inner diameter should be 30-200 μm larger than the outer diameter of the tube, preferably 30-100 μm larger than the outer diameter of the tube, the wall thickness of the membrane approximately 30-80 μm and the length of the membrane 0.2-4 cm.

For use of the catheter in blood special demands are called for in regard to the membrane. The dimension of the inner diameter is approximately 1000-3000 μm preferably approximately 1500 μm. The other blood-contacting surface of the membrane should be smooth reducing interactions with blood components, e.g. cells proteins. High roughness could lead to rupture of the blood cells and formation of a protein layer in the structure.

The smallest pores of the membrane should preferably be on the outside. Actually the word "pores" refer to the porous structure of a membrane, which means that they are not well-define channels rather openings in the membrane of varying width as one moves through the membrane.

The pore sizes preferably corresponding to a cut-off of approx 20,000-30,000 Da (measured in blood) if only glucose is to be measured. Low hydraulic permeability (Lp between $1 \times 10^{-4}$-$10 \times 10^{-4}$ cm$^3$/cm$^2$ sec bar) is correlated to the cut-off.

For targeting larger molecules there will be a need for a larger cut-off, and a higher hydraulic permeability.

The selective layer should preferably be thin allowing high mass transfer rates, i.e. the selective layer should create a low overall resistance. The selective layer is a deciding factor in the microdialysis as it determines what ions and compounds that are transported through that same layer. This is important as there need to be enough substance transferred to the perfusate during the microdialysis to be analysable.

The selective layer is situated on the outer circumference of the membrane facing the blood in the blood vessel. The selective layer is preferably a few μm and then there may be e.g. four layers having different characteristics. The stability of the membrane is attained by arranging amongst those four layers one layer which is less permeable than the surrounding layers but still not as selective as the selective layer. The less permeable layer will by nature be more stable/stiff in form. This layered structure allows for sufficient mechanical stability to build the system.

The structure of the membrane should preferably be hydrophilic allowing a spontaneous wettable membrane structure. The hydrophilic character of the membrane also provides for low adsorption of proteins, giving low fouling characteristics in direct blood application. Most of the membranes used in contact with blood have a domain structure on the surface of hydrophilic and hydrophobic domains, as is known within the art, on the surface facing the blood.

As the pore sizes are small there is also a need for wettability otherwise any transfer of ions or molecules might be hampered. The perfusate liquid should make good contact with the membrane allowing for the dialysis to take place.

The surface must be highly biocompatible, i.e. low thrombogenic surface. This is a function of the domain structure on the surface. This fact is known within the art.

Although the present invention has been described in connection with preferred embodiments thereof, it will be appreciated by those skilled in the art that additions, deletions, modifications and substitutions not specifically described may be made without departing from the spirit and scope of the invention as defined in the appended claims.

The invention claimed is:

1. A microdialysis catheter comprising a multilumen tube and a tubular membrane, said tube including two longitudinally arranged inner flow channels, said two longitudinally arranged inner flow channels representing an in-flow channel and an outflow channel, respectively, said flow channels extending from a proximal end of the tube to a distal end of the tube, wherein through-holes are provided, one from each of said two flow channels to the outside of said tube, said flow channels are blocked for passage of liquid distally of the respective through-holes, and the tubular membrane is arranged circumferentially around the tube such as to cover the two through-holes, wherein said tubular membrane is sealingly fastened to the tube, thereby forming a single dialysis chamber arranged between the tube and the tubular membrane and extending around their respective circumferences, wherein the flow channels are adapted to provide the same flow rate for the total in-flow, the total out-flow and the dialysis chamber flow, thus allowing a flow rate of 1-15 μl/minute, and wherein the tubular membrane is arranged such as to have a selective layer on the outer circumference of the tubular membrane to allow microdialysis of a target analyte.

2. A microdialysis catheter according to claim 1, comprising at least one further channel in the multilumen tube, said further channel extending between the proximal end of the tube to the distal end of the tube, said further channel adapted to house guide means and/or pressure measurement means and/or sampling/delivering means.

3. A microdialysis catheter according to claim 1, wherein the tube comprises extruded biocompatible polymeric material.

4. A microdialysis catheter according to claim 1, wherein the tubular membrane has a wall thickness of approximately 20-100 μm.

5. A microdialysis catheter according to claim 1, wherein the tubular membrane has a wall thickness of approximately 30 to 80 μm.

6. A microdialysis catheter according to claim 1, wherein the inner diameter of the tubular membrane is approximately 1000-3000 μm.

7. A microdialysis catheter according to claim 1, wherein the inner diameter of the tubular membrane is approximately 1000-2000 μm.

8. A microdialysis catheter according to claim 1, comprising means for detection of the position of the catheter, said means responsive to ultra sound while using the same for microdialysis purposes.

9. A microdialysis catheter according to claim 1, comprising means for detection of the position of the catheter, said means operable to impart opaqueness to X-rays to the catheter such that it is detectable using X-rays while using the catheter for microdialysis purposes.

10. A microdialysis catheter according to claim 1, wherein the total in-flow rate, the total out-flow rate and the dialysis chamber flow rate have the same rate, and the rate is 1-15 μl/minute.

11. A method of making a microdialysis catheter according to claim 1, comprising
   extruding a multilumen tube, said tube including two longitudinally arranged inner flow channels, said flow channels extending from a proximal end of the tube to the distal end of the tube,
   providing in said two flow channels through-holes, one from each of said two flow channels to the outside of said tube,
   blocking said flow channels for passage of liquid distally of the respective through-holes,
   arranging a tubular membrane circumferentially around the tube such as to cover the at two through-holes,
   sealingly fastening said tubular membrane to the tube thereby forming a single dialysis chamber arranged between the tube and the tubular membrane and extending around their respective circumferences, wherein the tubular membrane is arranged such as to have a selective layer on the outer circumference of the tubular membrane to allow microdialysis of a target analyte.

12. A method according to claim 11 in which at least one further channel in the tube is provided during the extrusion.

13. A microdialysis catheter according to claim 1, wherein the longitudinally arranged inner flow channels have tubular walls distinct from a wall of the multilumen tube.

\* \* \* \* \*